US006207424B1

(12) United States Patent
Chou et al.

(10) Patent No.: US 6,207,424 B1

(45) Date of Patent: Mar. 27, 2001

(54) SELF-PRIMED AMPLIFICATION SYSTEM

(75) Inventors: Quin Chou, Daly City; Joe Maa, San Bruno; Charlie Chang, Saratoga, all of CA (US)

(73) Assignee: Maxim Biotech, Inc., South San Francisco, CA (US)

( * ) Notice: Subject to any disclaimer, the term of this patent is extended or adjusted under 35 U.S.C. 154(b) by 0 days.

(21) Appl. No.: 09/447,942

(22) Filed: Nov. 23, 1999

(51) Int. Cl.$^7$ .................................................... C12P 19/34

(52) U.S. Cl. ........................... 435/91.1; 435/6; 435/91.2; 536/24.3; 536/24.33; 536/25.3

(58) Field of Search ................................. 435/91.1, 91.2, 435/6; 514/44; 536/24.3, 24.33, 25.3

(56) References Cited

U.S. PATENT DOCUMENTS 5,932,450 * 8/1999 Dattagupta et al. ..................... 435/6

* cited by examiner

*Primary Examiner*—W. Gary Jones
*Assistant Examiner*—Janell E. Taylor
(74) *Attorney, Agent, or Firm*—Townsend and Townsend and Crew LLP

(57) ABSTRACT

Disclosed are methods and compositions for copying a target nucleic acid using a self-priming primer. Single and different target nucleic acids can be copied using the disclosed methods and compositions.

52 Claims, 6 Drawing Sheets

A: Single SNAP Primer

Sense, target-specific binding domain Non-target, antisense primer binding domain Non-target, sense primer binding domain Antisense, target-specific binding domain

B: Two SNAP Primers

Sense, target-specific binding domain Non-target, antisense primer binding domain Non-target, sense primer binding domain Antisense, target-specific binding domain

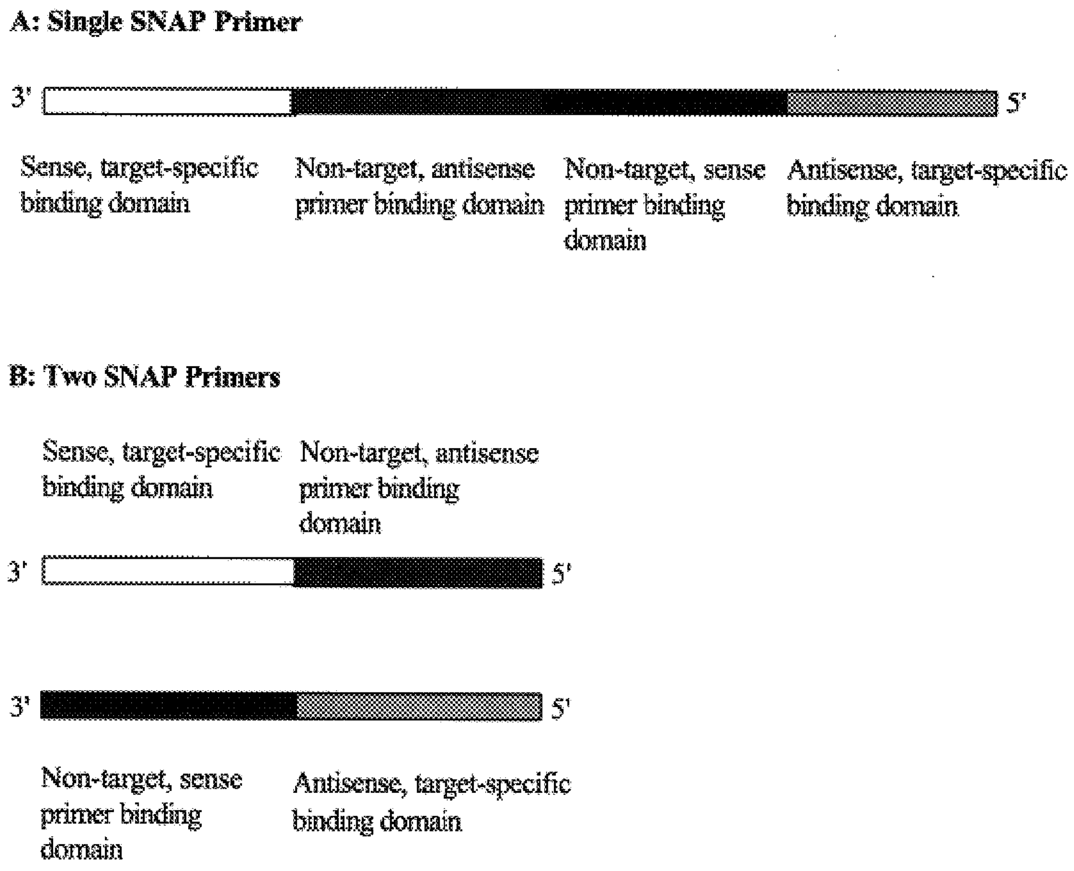

Figure 1

SELF-PRIMED AMPLIFICATION SYSTEM

CROSS-REFERENCE TO RELATED APPLICATIONS

[Not Applicable]

STATEMENT AS TO RIGHTS TO INVENTIONS MADE UNDER FEDERALLY SPONSORED RESEARCH AND DEVELOPMENT

[Not Applicable]

FIELD OF THE INVENTION

This invention relates to the field of copying a nucleic acid. An improved method of copying a nucleic acid with a self-priming primer is provided. Methods for using the self-priming primer to copy single and different target nucleic acids are described.

BACKGROUND OF THE INVENTION

Methods for copying nucleic acids provide useful tools for the detection of human pathogens, the detection of human genetic polymorphisms, molecular cloning, the detection of RNA and DNA sequences, sequencing of nucleic acids, and the like. In particular, the polymerase chain reaction (PCR) has become an important tool in the cloning of DNA sequences, forensics, paternity testing, pathogen identification, disease diagnosis, and other useful methods where the copying of a nucleic acid sequence is desired. See e.g., *PCR Technology: Principles and Applications for DNA Amplification* (Erlich, ed., 1992); *PCR Protocols: A Guide to Methods and Applications* (Innis et al., eds, 1990).

PCR permits the copying of a target nucleic acid. Briefly, a target nucleic acid, e.g. DNA, is combined with a sense and antisense primers, dNTPs, DNA polymerase and other reaction components. See Innis et al. The sense primer can anneal to the antisense strand of the DNA target. The antisense primer can anneal to the sense strand of the DNA target, downstream of where the sense primer anneals to the DNA target. In the first round of amplification, the DNA polymerase extends the antisense and sense primers that are annealed to the target nucleic acid. The first strands are synthesized as long strands of indiscriminate length. In the second round of amplification, the antisense and sense primers anneal to the parent target nucleic acid and to the complementary sequences on the long strands. The DNA polymerase then extends the annealed primers to form strands of discrete length that are complementary to each other. The subsequent rounds serve to predominantly amplify the DNA molecules of the discrete length.

The sense and antisense primers, however, lack the ability to self-prime. That is, the primers are not able to generate an oligonucleotide from their own sequence during amplification that will lead to the desired product. Another drawback of traditional PCR is that artifacts can be generated from mis-priming and primer dimerization. Those artifacts can be exacerbated in traditional multiplex PCR. Multiple sets of primers increase the possibility of primer complementarity at the 3'-ends, leading to primer-dimer formation. These artifacts deplete the reaction of dNTPs and primers and outcompete the multiplex amplicons for DNA polymerase. Such artifacts can be reduced by careful primer design and the use of "hot start" PCR. See Chou, Q. et al (1992) *Nucleic Acids Research,* 20: 1717–1723. It is increasingly difficult to eliminate all interactions that promote the mis-priming and primer dimerization, however, in a multiplex amplification as the reaction may contain many primers at high concentration.

Additionally, in a multiplex amplification, it is desirable that the amplification of different targets is quantitative, i.e., that the amplification accurately reflects the true ratio of target sequences in the sample. The data obtained using traditional multiplex PCR, however, is at best semi-quantitative. Amplification of sets of amplicons of varying lengths and GC-content may show preferential amplification of the shortest length and lowest GC-content amplicon. Further, differences in the yields of unequally amplified fragments are enhanced with each cycle. Multiplex PCR has been observed to suppress the amplification of one amplicon in preference for another amplicon. A number of factors are involved. For example, when a multiplex PCR involves different priming events for different target sequences, the relative efficiency of these events may vary for different targets. This can be due to the differences in thermodynamic structure stability and hybridization kinetics among the various primers used. Moreover, if the kinetics of product strand renaturation differ for different targets, the extent of competition with priming events will not be the same for all targets.

Accordingly, there is a need for compositions and methods that are less likely to produce variable and erroneous signals in multiplex assays. The present invention solves these problems and provides useful methods and compositions for carrying out a self-primed nucleic acid replication.

SUMMARY OF THE INVENTION

The present invention provides methods and compositions for copying a target nucleic acid using a self-primed amplification system to copy a single or different target nucleic acid sequences.

In one aspect, the present invention provides for a composition of a self-priming nucleic acid polymerase (SNAP) primer for copying a target nucleic acid comprising four domains of nucleic acid sequences. The domains are aligned in the following order from 3' to 5': i. a sense, target-specific binding domain; ii. a non-target, antisense primer binding domain; iii. a non-target sense primer binding domain; iv. an antisense, target-specific binding domain. The sequence of domain iv, the antisense, target-specific binding domain complements a sense sequence of the target which lies upstream of the target sequence complementary to the sense, target-specific binding domain.

In another aspect, the present invention provides for a mixture of amplification primers composed of first and second primers for copying a target nucleic acid. The first primer is comprised of two domains of nucleic acid sequences in the following order from 3' to 5': i. a sense, target-specific binding domain; and ii. a non-target, antisense primer binding domain. The second primer is comprised of two domains of nucleic acid sequences in the following order from 3' to 5': i. a non-target sense primer binding domain; and ii. an antisense, target-specific binding domain. The sequence of the antisense, target-specific binding domain complements a sense sequence of the target nucleic acid which lies upstream of the target nucleic acid sequence complementary to the sense, target-specific binding sequence.

In another aspect, the present invention provides for a mixture of nucleic acid primers for copying a target nucleic acid comprising a primer mixture selected from a group consisting of three different members. The first member is comprised of a primer comprising two domains of nucleic acid sequences in the following order from 3' to 5': i. a sense, target-specific binding domain; ii. a non-target, antisense primer binding domain; and a primer having 3' sequence identity to the sequence of the non-target, antisense primer binding domain. The second member is comprised of a primer comprising two domains of nucleic acid sequences in the following order from 3' to 5': i. a non-target sense primer binding domain; ii. an antisense, target-specific binding domain wherein the sequence of the domain complements a sense sequence of the target nucleic acid which lies upstream of the target nucleic acid sequence complementary to the sense, target-specific binding sequence; and a primer complementary to the non-target sense primer binding domain. The third member of the group is a combination of four primers making up the first and second members of the group.

In another aspect, the present invention provides for a method of copying a target nucleic acid. In the first step, the following components are combined in an aqueous solution: a target nucleic acid, a nucleic acid polymerase, a molar excess of dNTPs, a non-target antisense primer, a non-target sense-primer, and self-priming nucleic acid polymerase (SNAP) primers for copying a target nucleic acid. The SNAP primers comprise four domains of nucleic acid sequences in the following order from 3' to 5': i. a sense, target-specific binding domain; ii. a non-target, antisense primer binding domain; iii. a non-target sense primer binding domain; iv. an antisense, target-specific binding domain, wherein the sequence of the domain complements a sense sequence of the target nucleic acid which lies upstream of the target nucleic acid sequence complementary to the sense, target-specific binding sequence. The SNAP primer(s) can be (a) two primers where the first primer is a primer where domains i and ii are joined together and where the second primer is a primer where domains iii and iv are joined together; or (b) a single primer where domains i, ii, iii, and iv are all joined together. In the next step, the SNAP primers are allowed to bind to the target nucleic acid and to the non-target sense primer, so as to permit the nucleic acid polymerase to extend the primers to create: i. a nascent sense primer having a non-target primer sequence and a target-specific binding sequence having identity to a sense sequence of the target nucleic acid which lies upstream of the target nucleic acid sequence complementary to the sense, target-specific binding sequence of the SNAP primer; and ii. a long SNAP extension (antisense) product. The nucleic acid strands are then denatured. After denaturation, the to permit the nucleic acid polymerase to extend the nascent sense primer to yield a long, nascent primer extension (sense) product having a non-target antisense primer binding sequence. Then, the nucleic acid strands are denatured again. The non-target antisense primer is allowed to bind to the long, nascent primer extension (sense) product to permit the nucleic acid polymerase to extend the non-target antisense primer to yield a short, antisense primer extension (antisense) product terminating in a non-target sense primer binding sequence. The nucleic acid strands are once again subjected to a denaturing step. Next, the non-target sense primer is allowed to bind to the short primer extension (antisense) product to yield a short non-target primer extension (sense) product terminating in a non-target antisense primer binding sequence. After that step, the non-target primers are allowed to repetitively bind to the short extension products in a series of polymerase extension and denaturation cycles to amplify the target nucleic acid.

In another aspect, the present invention provides for a method of copying at least 2 different target nucleic acids. In the first step, the following components are combined in an aqueous solution: at least 2 different target nucleic acids, nucleic acid polymerase, a molar excess of dNTPs, non-target antisense primers, non-target sense-primers, and self-priming nucleic acid polymerase (SNAP) primers for copying at least 2 different target nucleic acids, the primers comprising four domains of nucleic acid sequences in the following order from 3' to 5': i. a sense, target-specific binding domain; ii. a non-target, antisense primer binding domain; iii. a non-target sense primer binding domain; iv. an antisense, target-specific binding domain, wherein the sequence of the domain complements a sense sequence of the target nucleic acid which lies upstream of the target nucleic acid sequence complementary to the sense, target-specific binding sequence. The SNAP primer(s) can be (a) two primers where the first primer is a primer where domains i and ii are joined together and where the second primer is a primer where domains iii and iv are joined together; or (b) a single primer where domains i, ii, iii, and iv are all joined together. In the next step, the SNAP primers are allowed to bind to the target nucleic acids and to the non-target sense primer, so as to permit the nucleic acid polymerase to extend the primers to create: i. nascent sense primers having a non-target primer sequence and a target-specific binding sequence having identity to a sense sequence of the target nucleic acid which lies upstream of the target nucleic acid sequence complementary to the sense, target-specific binding sequence of the SNAP primer; and ii. long SNAP extension (antisense) products. The nucleic acid strands are then denatured. After denaturation, the nascent sense primers are allowed to bind to the long, SNAP extension (antisense) products to permit the nucleic acid polymerase to extend the nascent sense primers to yield long, nascent primer extension (sense) products having a non-target antisense primer binding sequence. The nucleic acid strands are then denatured again. Then, the non-target antisense primers are allowed to bind to the long, nascent primer extension (sense) products to permit the nucleic acid polymerase to extend the non-target antisense primers to yield short, antisense primer extension (antisense) products terminating in a non-target sense primer binding sequence. The nucleic acid strands are then denatured again. Next, the non-target sense primers are allowed to bind to the short primer extension (antisense) products to yield a short non-target primer extension (sense) products terminating in a non-target antisense primer binding sequence. After that step, the non-target primers are allowed to repetitively bind to the short extension products in a series of polymerase extension and denaturation cycles to amplify the target nucleic acids.

In another aspect, the present invention provides for a kit comprising: a container having a self-priming nucleic acid polymerase (SNAP) primer for copying a target nucleic acid comprising four domains of nucleic acid sequences in the following order from 3' to 5': i. a sense, target-specific binding domain; ii. a non-target, antisense primer binding domain; iii. a non-target sense primer binding domain; iv. an antisense, target-specific binding domain, wherein the sequence of the domain complements a sense sequence of the target nucleic acid which lies upstream of the target nucleic acid sequence complementary to the sense, target-specific binding sequence. The SNAP primer can be: (a) two primers where the first primer is a primer where domains i and ii are joined together and where the second primer is a primer where domains iii and iv are joined together; or (b) a single primer where domains i, ii, iii, and iv are all joined together.

BRIEF DESCRIPTION OF THE DRAWINGS

FIG. 1 is a schematic of the architecture of a Self-priming Nucleic Acid Polymerase (SNAP) Primer. Part (A) shows a Single SNAP primer with the 4 domains. Part (B) shows the split SNAP primer.

TABLE I

| Primers and cDNAs | Lane #1 | Lane #2 | Lane #3 | Lane #4 | Lane #5 | Lane #6 |
|---|---|---|---|---|---|---|
| human Tcell cDNA | + | + | − | + | + | + |
| human brain cDNA | + | − | + | − | − | + |
| SPAS-BCL-1001 | − | + | + | − | − | + |
| SPAS-GAP-1001 | − | − | − | + | + | − |
| ADP-1002 | + | + | + | + | − | − |

Figure 5:
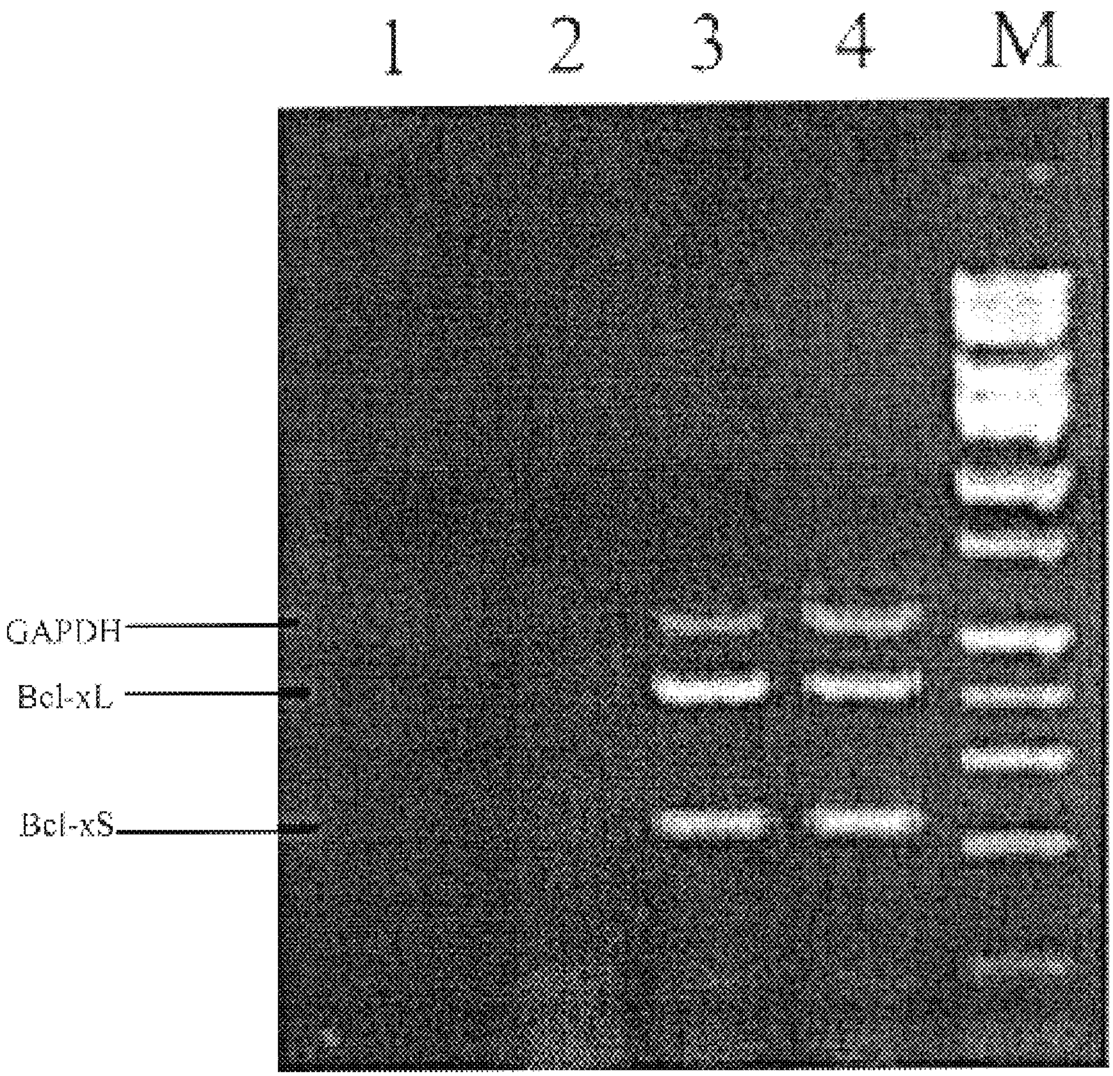

FIG. 5 is a gel photograph of the amplification of different cDNAs in a single reaction vessel using SNAP primers. A mixture of human brain cDNA and human T cell cDNA was amplified in a single tube using SNAP primers for bcl-xS, bcl-xL and GAPDH target sequences. The reactions were electrophoresed on a 2% agarose gel. The gel was stained with ethidium bromide. The primer and cDNA components for the respective lanes are shown in Table II. The lane denoted "M" is a marker lane containing a DNA ladder (Minnesota Molecular Hi-Lo™ DNA Marker, Cat. No. 1010).

TABLE II

| Primers and cDNAs | Lane #1 | Lane #2 | Lane #3 | Lane #4 |
|---|---|---|---|---|
| human Tcell cDNA and human brain cDNA | − | + | + | + |
| SPAS-BCL-1001 (SEQ. ID NO:1) | + | + | + | + |
| SPAS-GAP-1001 (SEQ. ID NO:2) | + | + | + | + |
| ADP-1002 | + | + | + | + |
| mM $MgCl_2$ | 3.5 | 1.5 | 2.5 | 3.5 |

Figure 6:
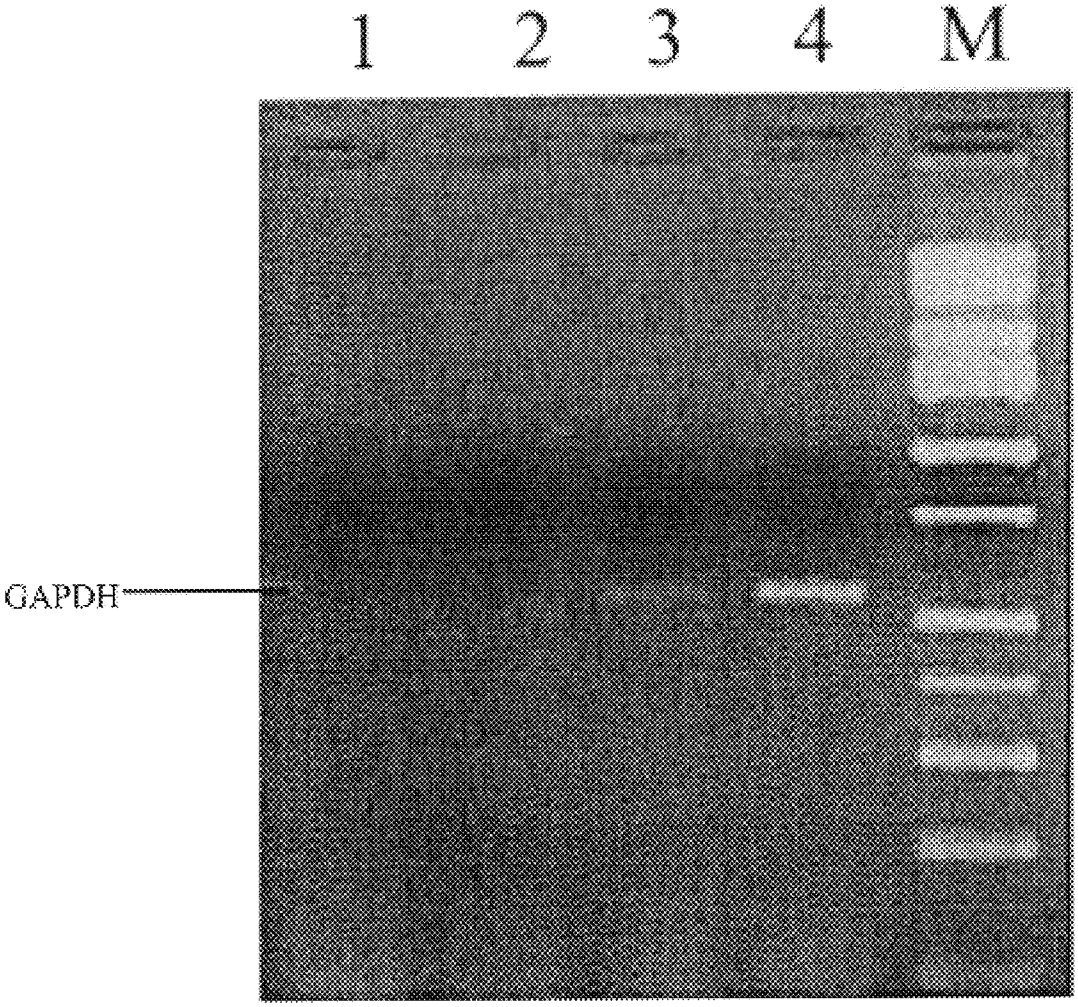

FIG. 6 is a gel photograph of the amplification of a single target RNA in a closed tube format using a SNAP primer. Total RNA from the cultured keratinocytes was reverse transcribed and subjected to amplification using the SPAS-GAP-1001 SNAP primer and the ADP-1002 primer. The reaction was electrophoresed on a 2% agarose gel. The gel was stained with ethidium bromide. The primer and cDNA components for the respective lanes are shown in Table II. The lane denoted "M" is a marker lane containing a DNA ladder (Minnesota Molecular Hi-Lo™ DNA Marker, Cat. No. 1010). The reaction components are shown in Table III. All of the reactions contained total RNA from keratinocytes.

TABLE III

| Reaction components | Lane #1 | Lane #2 | Lane #3 | Lane #4 |
|---|---|---|---|---|
| *C. therm.* Polymerase | + | + | − | + |
| Taq DNA polymerase | + | + | + | + |
| SPAS-GAP-1001 | + | − | + | + |
| ADP-1002 | − | + | + | + |

DEFINITIONS

As used herein, the following terms have the meanings ascribed to them unless specified otherwise.

The phrase "self-priming nucleic acid polymerase (SNAP) primer(s)" refers to a nucleic acid polymer(s) designed to copy a target nucleic acid in a polymerase/polymerase primer dependent amplification scheme where the primer serves as both a primer and as a template for the generation of a primer not originally in the starting reaction mixture.

The term "copying" refers to a process whereby a portion of a target nucleic acid is replicated. Unless specifically stated "copying" may refer to single replication or arithmetic, logarithmic, or exponential amplification.

The phrase "target nucleic acid" refers to a nucleic acid polymer that is sought to be copied. The "target nucleic acid(s)" can be isolated or purified from a cell, bacterium, protozoa, fungus, plant, animal, etc. Alternatively, the "target nucleic acid(s)" can be contained in a lysate of a cell, bacterium, protozoa, fungus, plant, animal, etc.

The term "domain" refers to a subsequence of the SNAP primer that has been assigned a specific function in the amplification process. Domains may be adjacent to each other or separated by nonfunctional bases. Alternatively, two or more of the domains may overlap each other.

The phrase "nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

The phrase "3' to 5'" refers to the directionality of a nucleic acid polymer. The 3' end is the terminus of a nucleic acid polymer wherein the 3' position is not linked to another nucleotide. The 5' end is the terminus of a nucleic acid polymer wherein the 5' position is free. The phrase "3' to 5'" refers to a direction of moving from the 3' end towards the 5' end.

The phrase "sense, target-specific binding domain" refers to a subsequence of a primer that is able to bind to the sense strand of the target nucleic acid. The "sense, target-specific binding domain" is complementary to a portion of the sense strand of the target nucleic acid.

The phrase "non-target, antisense primer binding domain" refers to a subsequence of a primer that is not complementary to the target nucleic acid and is able to bind to the "non-target antisense primer." The "non-target, antisense primer binding domain" is complementary to a portion of the "non-target antisense primer."

The phrase "non-target sense primer binding domain" refers to a subsequence of a primer that is not complementary to the target nucleic acid and is able to bind to the "non-target sense primer." The "non-target sense primer binding domain" is complementary to a portion of the "non-target sense primer."

The phrase "antisense, target-specific binding domain" refers to a subsequence of a primer that is able to bind to the antisense strand of the target nucleic acid. The "antisense, target-specific binding domain" is complementary to a portion of the antisense strand of the target nucleic acid upstream (i.e., 5') of where the "sense, target-specific binding domain" binds to the sense strand of the target nucleic acid.

The term "human pathogen" refers to an entity that causes a disease or disorder in humans. For example, a "human pathogen" may be, but is not limited to, a bacteria, a virus, a plant, or a protozoa.

The term "$T_m$ " refers to the mid-point melting temperature at which two nucleic acid polymers are found entirely bound and entirely separate. It should be appreciated that the actual value will vary in accord with the hybridization solution used. The $T_m$ can either be calculated by computer based upon their sequences or empirically determined by experimental determination.

The phrase "primer having 3' sequence identity to the sequence of the non-target, antisense primer binding domain" refers to a primer that is completely homologous in at least 5 nucleotides at the 3' end of the "non-target, antisense primer binding domain."

The phrase "amplification primer pairs" refers to oligonucleotides that flank the target region of a DNA that is being amplified.

The phrase "nucleic acid polymerase" refers to an enzyme that is able to catalyze substrate dependent DNA synthesis in a 3' direction using a primer, a target nucleic acid and dNTP's. The "nucleic acid polymerase" can use DNA as a primer and target nucleic acid (e.g., Taq DNA Polymerase). Alternatively the "nucleic acid polymerase" can use DNA as a primer and RNA as the target nucleic acid (e.g., reverse transcriptase).

The phrase "molar excess of dNTPs" refers to a solution in which the molar concentration of dNTPs exceeds the molar concentration of the amplification primers present in the reaction. The term "dNTPs" refers to deoxyribonucleotides. Such dNTPs can include G, A, C or T.

The phrase "non-target antisense primer" refers an oligonucleotide that is complementary to the "non-target, antisense primer binding domain" of a SNAP primer.

The phrase "non-target sense-primer" refers an oligonucleotide that is complementary to the "non-target, sense primer binding domain" of a SNAP primer.

The term "nascent sense primer" refers to an oligonucleotide that is generated in situ from a polymerase extension reaction in which the SNAP primer is used as a template and in which the newly generated oligonucleotide is used in a subsequent step to generate a longer nucleic acid extension product using the target DNA as a template. This primer includes a complement of domains iii and iv of the SNAP primer.

The phrase "long SNAP extension (antisense) product" refers to an amplification product generated by the 3' extension of domain i of the SNAP primer (in either a single or split configuration) when bound to a sense strand of a target nucleic acid (template). It is a "long" product because it does not have a precisely defined end or point of termination.

The phrase "denaturing the nucleic acid strands" refers to the melting or physical separation of a nucleic acid duplex.

The term "long, nascent primer extension (sense) product having a non-target antisense primer binding sequence" refers to an amplification product generated by the 3' extension of the nascent primer when its 3' complement to domain iv of the SNAP primer is bound to its complement on the long SNAP extension (antisense) product. It is a "long" product because the product's 3' end may include domain iv of the SNAP primer which will not be amplified in subsequent rounds of amplification.

The term "short, antisense primer extension (antisense) product terminating in a non-target sense primer binding sequence" refers to an amplification product generated from the 3' extension of the non-target antisense primer using the long, nascent primer extension (sense) product as a template. It is "short" because the end sequence is defined and the antisense primer is a part of its sequence.

The term "short non-target primer extension (sense) product terminating in a non-target antisense primer binding sequence" refers to the 3' extension product of the non-target antisense primer using the short antisense primer extension (antisense) product as a template.

The term "repetitively allowing the non-target primers to bind to the short extension products in a series of polymerase extension and denaturation cycles to amplify the target nucleic acid" refers to a controlled cycling of enzymatic generation of oligonucleic acids and strand separation.

The phrase "reverse transcriptase" refers to an enzyme that is able to catalyze the synthesis of DNA using a DNA primer and an RNA substrate.

The term "different" as it appears in the phrases "3 different SNAP primers", "3 different target nucleic acids" and "2 different target nucleic acids" refers to nucleic acid molecules that are not identical in their linear nucleic acid sequence.

The phrase "simultaneously copied in the same solution" refers to a process wherein different sequences of nucleic acids (targets) are replicated in the same reaction vessel at the same time.

The phrase "detecting step" refers to procedure that permits the quantification of the amplified product.

The term "homogenous assay" refers to an assay in which the reaction and detection steps take place in the same solution.

The term "detectable label" refers to a moiety that is attached through covalent or non-covalent means to the non-target antisense primer or said non-target sense-primer. A "detectable label" can be a radioactive moiety, a fluorescent moiety, a chemiluminescent moiety, etc.

The term "fluorescent label" refers to label that accepts radiant energy of one wavelength and emits radiant energy of a second wavelength.

DETAILED DESCRIPTION

Introduction

The present invention provides methods and compositions for copying target nucleic acids with a self-priming nucleic acid polymerase (SNAP) primer. These methods and compositions may be useful for the amplification and detection of nucleic acids of clinical importance.

Snap Primers

A. Architecture

The present invention discloses a self-priming nucleic acid polymerase (SNAP) primer compositions for copying a target nucleic acid. One embodiment of such a SNAP primer is a single contiguous primer. See FIG. 1A. This single SNAP primer is composed of four domains. The domains are aligned in the following order from 3' to 5': (i.) a sense, target-specific binding domain; (ii). a non-target, antisense primer binding domain; (iii). a non-target sense primer binding domain; and (iv). an antisense, target-specific binding domain.

Alternatively, another embodiment of the present invention is a split SNAP primer composed of a first primer and a second primer. See FIG. 1B. The first primer is comprised of two domains of nucleic acid sequences in the following order from 3' to 5': (i). a sense, target-specific binding domain; and (ii). a non-target, antisense primer binding domain. See FIG. 1B. The second primer is comprised of two domains of nucleic acid sequences in the following order from 3' to 5': (i). a non-target sense primer binding domain; and (ii). an antisense, target-specific binding domain. See FIG. 1B.

B. Domains

The domains are subsequences of the SNAP primer(s) that have been assigned a specific function in the amplification process. These domains may be adjacent to each other or separated by nonfunctional bases. Alternatively, two or more domains may overlap each other.

The sense, target-specific binding domain.

The sense, target-specific binding domain is domain i of the single SNAP primer or domain i of the first primer of the split SNAP primer. See FIG. 1. This domain is able to bind to the sense strand of the target nucleic acid. The sense, target-specific binding domain is complementary to a portion of the target nucleic acid. One of ordinary skill will recognize many ways to design the oligonucleotide sequence of a domain, e.g., the sense, target-specific binding domain, to be complementary to and thus be able to bind to a portion of the target nucleic acid. The sense, target-specific binding domain can be designed by one of ordinary skill in the art to have a $T_m$ of about a particular temperature using a computer model or experimental techniques. Preferably, the $T_m$ of the sense, target-specific binding domain is at least 62° C. for its complementary sequence on the target nucleic acid.

The non-target, antisense primer binding domain.

The non-target, antisense primer binding domain is domain ii of the single SNAP primer or domain ii of the first primer of the split SNAP primer. See FIG. 1. This domain is able to bind to the non-target antisense primer. The non-target, antisense primer binding domain is complementary to a portion of the non-target antisense primer. One of ordinary skill will recognize many ways to design the oligonucleotide sequence of the non-target, antisense primer binding domain to be complementary to and thus be able to bind to a portion of the non-target antisense primer. The non-target, antisense primer binding domain can be designed by one of ordinary skill in the art to have a $T_m$ of about a particular temperature using a computer model or experimental techniques. Preferably, the $T_m$ of the non-target, antisense primer binding domain is at least 62° C. for its complementary sequence on the non-target, antisense primer. More preferably, the $T_m$ is higher than the $T_m$ for the target-specific binding domains and their complementary sequences on the target nucleic acid.

The non-target sense primer binding domain.

The non-target sense primer binding domain is domain iii of the single SNAP primer or domain i of the second primer of the split SNAP primer. See FIG. 1. This domain is able to bind to the non-target sense primer. The non-target sense primer binding domain is complementary to a portion of the non-target sense primer. One of ordinary skill will recognize many ways to design the oligonucleotide sequence of the non-target sense primer binding domain to be complementary to and thus be able to bind to a portion of the non-target sense primer. The non-target, antisense primer binding domain can be designed by one of ordinary skill in the art to have a $T_m$ of about a particular temperature using a computer model or experimental techniques. Preferably the $T_m$ for the non-target sense primer binding domain is at least 62° C. for its complementary sequence on the non-target sense primer. More preferably, the $T_m$ is higher than the $T_m$ for the target-specific binding domains and their complementary sequences on the target nucleic acid.

The antisense target-specific binding domain.

The antisense, target-specific binding domain is domain iv of the single SNAP primer or domain ii of the second primer of the split SNAP primers. See FIG. 1. This domain is able to bind to the antisense strand of the target nucleic acid. The antisense, target-specific binding domain is complementary to a portion of the target nucleic acid. The antisense, target-specific binding domain binds to the antisense strand of the target nucleic acid “upstream” (i.e., 5' to), of the location on the sense strand of the target nucleic acid that is complementary to the sense, target-specific binding domain. One of ordinary skill will recognize many ways to design the antisense, target-specific binding domain to be complementary to and thus be able to bind to a portion of the target nucleic acid. The antisense, target-specific binding domain can be designed by one of ordinary skill in the art to have a $T_m$ of about a particular temperature using a computer model or experimental techniques. Preferably the $T_m$ for the antisense, target-specific binding domain is at least 62° C. for its complementary sequence on the target nucleic acid.

Examples of SNAP Primers

Figure 2:
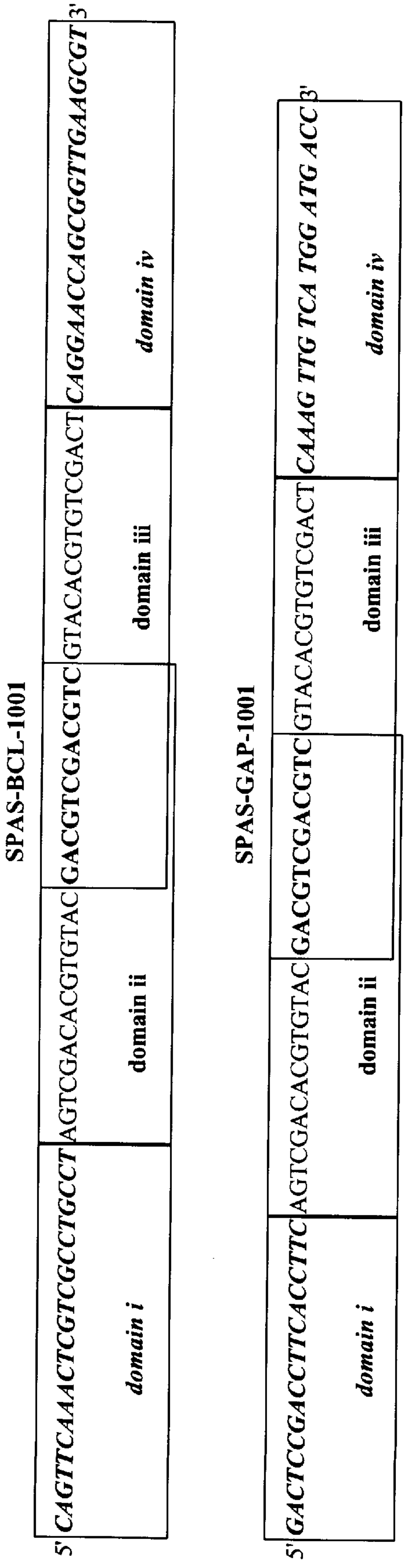
FIG. 2 shows the nucleotide sequence of Single SNAP primers SPAS-BCL-1001 and SPAS-GAP-1001, overlaid with the four domains.
Figure 3:
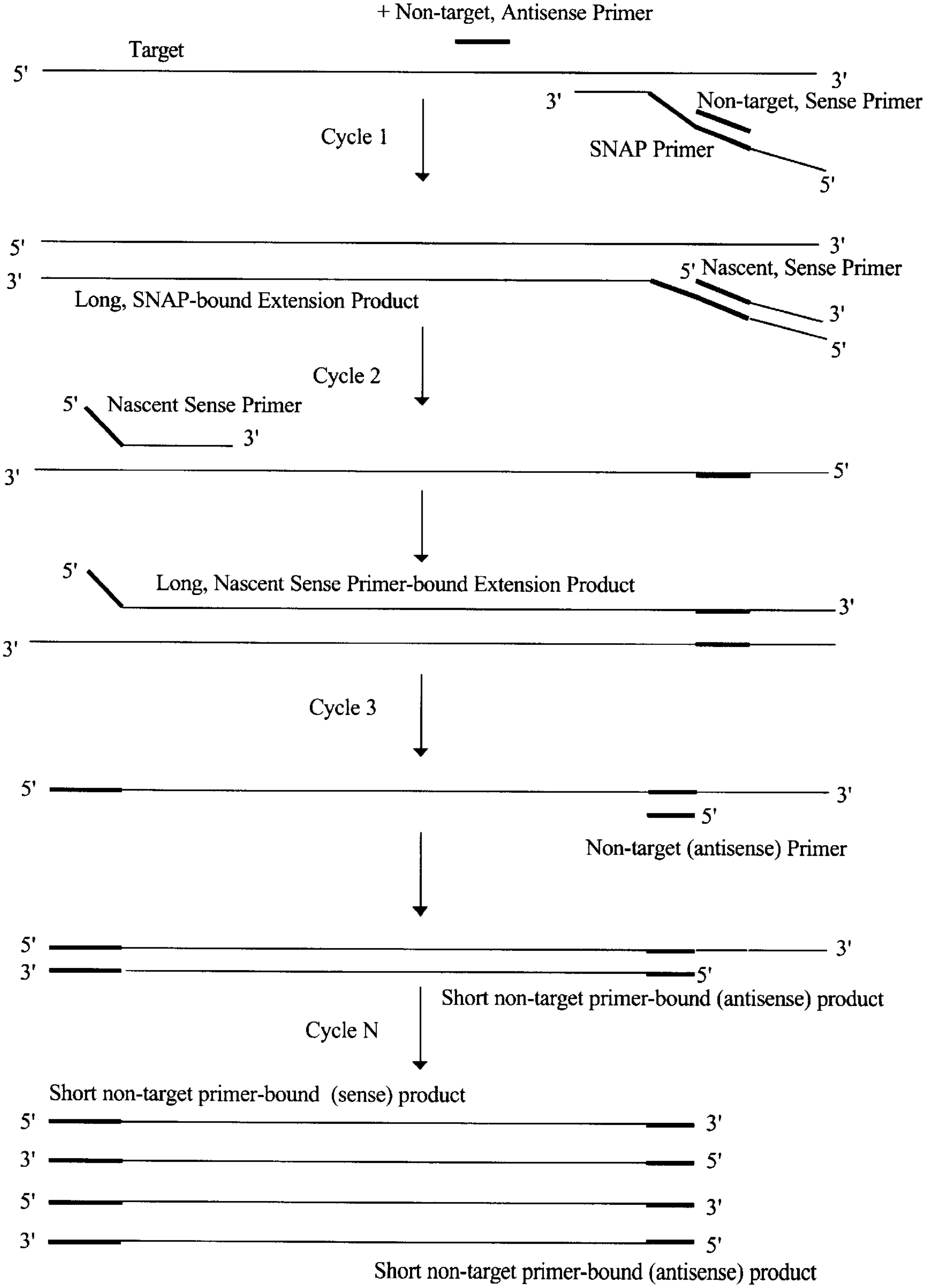
FIG. 3 is a schematic of the self-primed amplification of a target nucleic acid using a single SNAP primer, non-target antisense primer, and a non-target sense primer.

The nucleic acid sequence of the single SNAP primers SPAS-BCL-1001 (87 nucleotides) and SPAS-GAP-1001 (81 nucleotides) are depicted in FIG. 2 overlaid with the demarcations of the respective domains. The SPAS-BCL-1001 SNAP primer (SEQ ID NO: 1) is directed towards bcl-xS and bcl-xL sequences. The SPAS-GAP-1001 (SEQ ID NO: 2) is directed towards GAPDH sequences. In these particular embodiments, SPAS-BCL-1001 and SPAS-GAP-1001, domains ii and iii overlap. The 5' region of domain ii overlaps with the 3' region of domain iii by 12 nucleotides for these two embodiments. See FIG. 2. Also in these two particular embodiments (SPAS-BCL-1001 and SPAS-GAP-1001), domain ii and domain iii are complementary and would be able to adopt a hairpin structure. When the target nucleic acid is DNA, the SNAP primers are comprised of DNA. Alternatively, when the target nucleic acid is comprised of RNA, the second SNAP primer of a split SNAP primer can be RNA, if reverse transcriptase is used to synthesize the nascent primers.

Non-target sense primer and the Non-target antisense primer.

Amplification of target nucleic acids also requires a non-target sense primer and a non-target antisense primer. The non-target sense primer and the non-target antisense primer may be the same sequence if the non-target sense primer can anneal to domain ii of the SNAP primer or domain ii of the first primer of the split SNAP primer, and if the non-target antisense primer can anneal to domain iii of the SNAP primer or domain i of the second primer of the split SNAP primer. Thus, the same primer sequence can function as a non-target sense and a non-target antisense primer. For example, the 27 nucleotide primer ADP-1002

(SEQ ID NO: 3) is such a primer, when used in conjunction with the SPAS-GAP-1001 or SPAS-BCL-1001 primer. Those of skill in the art will be able to design non-target primers of varying sequences and lengths that would be able to function in the amplification process using the methods and compositions of the present invention.

C. Target DNA sequences

Target DNA sequences may be a DNA isolated from a biological source, e.g., a bacterium, a cell, a plant, etc. Methods are known for lysing organisms and preparing extracts or purifying DNA. See, *Current Protocols in Molecular Biology* (Ausubel et al, eds., 1994)). Also, total RNA or polyA+RNA can be reverse transcribed to produce cDNA which can serve as the target DNA. Alternatively, the target DNA sequences may be isolated using a variety of techniques. In general, the nucleic acid sequences encoding genes of the target DNA sequences of interest are cloned from cDNA and genomic DNA libraries by hybridization with a probe, or isolated using amplification techniques with oligonucleotide primers. Preferably, sequences from human pathogens, more preferably human sequences are used. For example, target DNA sequences are typically isolated from mammalian nucleic acid (genomic or cDNA) libraries by hybridizing with a nucleic acid probe, the sequence of which can be derived from the gene of the target DNA sequence being cloned.

Amplification techniques using primers can also be used to amplify and isolate, a nucleic acid encoding the target DNA sequence from DNA or RNA (see, e.g., Dieffenfach & Dveksler, (1995) *PCR Primer: A Laboratory Manual*). These primers can be used, e.g., to amplify either the full length sequence or a probe of one to several hundred nucleotides, which is then used to screen a mammalian library for the full-length nucleic acid of choice. For example, degenerate primer sets, can be used to isolate the relevant nucleic acids encoding the target DNA sequences. Nucleic acids can also be isolated from expression libraries using antibodies as probes. Such polyclonal or monoclonal antibodies can be raised using the predicted amino acid sequence of the target DNA sequence being cloned.

Polymorphic variants and alleles that are substantially identical to the gene of the target DNA sequence of choice can be isolated using nucleic acid probes, and oligonucleotides under stringent hybridization conditions, by screening libraries. Alternatively, expression libraries can be used to clone variant genes of the target DNA sequence being cloned such as, polymorphic variants, interspecies homologs, and alleles, by detecting expressed homologs immunologically with antisera or purified antibodies made against the predicated amino acid sequence of the target DNA sequence.

To make a cDNA library, one should choose a source that is rich in the mRNA of the target DNA sequence of interest. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, (1983) *Gene* 5:263–269; Sambrook et al., ($2^{nd}$ ed. 1989) *Molecular Cloning, A Laboratory Manual*; and Ausubel et al.

For a genomic library, the DNA is extracted from the tissue and either mechanically sheared or enzymatically digested to yield fragments of about 12–20 kb. The fragments are then separated by gradient centrifugation from undesired sizes and are constructed in non-lambda expression vectors. These vectors are packaged in vitro. Recombinant phage are analyzed by plaque hybridization as described in Benton & Davis, (1977) *Science* 196:180–182. Colony hybridization is carried out as generally described in Grunstein et al., (1975) *Proc. Natl. Acad. Sci. USA.,* 72:3961–3965.

An alternative method of isolating a nucleic acid and its homologs combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of target DNA sequences directly from mRNA, from cDNA, from genomic libraries or cDNA libraries. Degenerate oligonucleotides can be designed to amplify target DNA sequence homologs using the known sequences that encode the target DNA sequence. Restriction endonuclease sites can be incorporated into the primers. Polymerase chain reaction or other in vitro amplification methods may also be useful, for example, to clone nucleic acid sequences that code for the target DNA sequence proteins to be expressed. Genes amplified by the PCR reaction can be purified from agarose gels and cloned into an appropriate vector.

Synthetic oligonucleotides can be used to construct recombinant genes for use as probes or for expression of the target DNA sequence proteins. Oligonucleotides can be chemically synthesized according to the solid phase phosphoramidite triester method first described by Beaucage & Caruthers, (1981) *Tetrahedron Letts.* 22:1859–1862, using an automated synthesizer, as described in Van Devanter et al., (1984) *Nucleic Acids Res.* 12: 6159–6168. Purification of oligonucleotides is typically by either native acrylamide gel electrophoresis or by anion-exchange HPLC as described in Pearson & Reanier, (1983) *J. Chrom.* 255:137–149. The sequence of the cloned genes and synthetic oligonucleotides can be verified after cloning using, e.g., the chain termination method for sequencing double-stranded templates of Wallace et al., (1981) *Gene* 16:21–26. This method is performed using a series of overlapping oligonucleotides usually 40–120 bp in length, representing both the sense and non-sense strands of the gene. These DNA fragments are then annealed, ligated and cloned.

Alternatively, amplification techniques can be used with precise primers to amplify a specific subsequence of the target DNA sequence encoded by the nucleic acid. The specific subsequence is then ligated into a vector.

D. Target RNA sequences

RNA target sequences that are amplified using the methods and compositions of the present invention may be a single RNA target or different RNA targets. The RNA can be isolated as total RNA from a cell, bacterium, virus etc. See, Ausubel et al. The total RNA may be subsequently purified as poly A+RNA or purified in a different manner to isolate certain species of interest. See Ausubel et al. Alternatively, the target RNA can be transcribed in vitro and used in the present invention. The RNA target sequence could also be reverse transcribed into cDNA and copied in a closed tube format using the methods described herein for copying a target DNA. Or the RNA target sequence can be reverse transcribed and then separately added to a reaction mix for amplification.

Amplification of a Single Target DNA Using a SNAP Primer or a Split SNAP Primer

In a single reaction vessel, the following components are combined in an aqueous solution: target nucleic acid, nucleic acid polymerase, a molar excess of dNTPs, non-target antisense primers, non-target sense-primers, and self-priming nucleic acid polymerase (SNAP) primers for copying a target nucleic acid. The SNAP primer can be a single SNAP primer or a split SNAP primer. Preferably, the reaction can be carried out in a thermal cycler to facilitate incubation times at a the desired temperatures.

A. Reaction components

Oligonucleotide Primers.

The oligonucleotides that are used in the present invention (e.g., the SNAP primers and non-target primers) as well as oligonucleotides designed to detect amplification products can be chemically synthesized, as described above. These oligonucleotides can be labeled with radioisotopes, chemiluminescent moieties, or fluorescent moieties in a covalent or non-covalent manner. Such labels are useful for the characterization and detection of amplification products using the methods and compositions of the present invention.

Buffer.

Buffers that may be employed are borate, phosphate, carbonate, barbital, Tris, etc. based buffers. See Rose et al., U.S. Pat. No. 5,508,178. The pH of the reaction should be maintained in the range of about 4.5 to about 9.5. See U.S. Pat. No. 5,508,178. The standard buffer used in amplification reactions is a Tris based buffer between 10 and 50 mM with a pH of around 8.3 to 8.8. See Innis et al.

Salt concentration.

The concentration of salt present in the reaction can affect the ability of primers to anneal to the target nucleic acid. See Innis et al. Potassium chloride is added up to a concentration of about 50 mM to the reaction mixture to promote primer annealing. Sodium chloride can also be added to promote primer annealing. See Innis et al.

Magnesium ion concentration.

The concentration of magnesium ion in the reaction can be critical to amplifying the desired sequence(s). See Innis et al. Primer annealing, strand denaturation, amplification specificity, primer-dimer formation, and enzyme activity are all examples of parameters that are affected by magnesium concentration. See Innis et al. Amplification reactions should contain about a 0.5 to 2.5 mM magnesium concentration excess over the concentration of dNTPs. The presence of magnesium chelators in the reaction can affect the optimal magnesium concentration. A series of amplification reactions can be carried out over a range of magnesium concentrations to determine the optimal magnesium concentration. The optimal magnesium concentration can vary depending on the nature of the target nucleic acid(s) and the primers being used, among other parameters.

Deoxynucleotide Triphosphate concentration.

Deoxynucleotide triphosphates (dNTPs) is added to the reaction to a final concentration of about 20 $\mu$M to about 300 $\mu$M. Each of the four dNTPs (G, A, C, T) should be present at equivalent concentrations. See Innis et al.

Nucleic acid polymerase.

A variety of DNA dependent polymerases are commercially available that will function using the methods and compositions of the present invention. For example, Taq DNA Polymerase may be used to amplify target DNA sequences. Also, a reverse transcriptase can be used in certain embodiments of the present invention. Reverse transcriptases, such as the thermostable *C. therm* polymerase from Roche, are also widely available on a commercial basis.

Other agents.

Assorted other agents are sometime added to the reaction to achieve the desired results. For example, DMSO can be added to the reaction, but is reported to inhibit the activity of Taq DNA Polymerase. But DMSO has been recommended for the amplification of multiple target sequences in the same reaction. See Innis et al. Stabilizing agents such as gelatin, bovine serum albumin, and non-ionic detergents (e.g. Tween-20) are commonly added to amplification reactions. See Innis et al.

B. Amplification Using SNAP primers.

In the first step, the SNAP primers anneal to the target nucleic acid and to the non-target sense primer. The nucleic acid polymerase extends the primers to create: (i). a nascent sense primer having a non-target primer sequence and a target-specific binding sequence having identity to a sense sequence of the target nucleic acid which lies upstream of the target nucleic acid sequence complementary to the sense, target-specific binding sequence of the SNAP primer; and (ii). a long SNAP extension (antisense) product. The extension steps can be carried out in a thermal cycler at a temperature that will permit the DNA polymerase to bind to the primer-template complex and catalyze the polymerization of DNA. The nucleic acid strands are then denatured. Typically, denaturation is achieved by incubating the reaction mixture at a temperature sufficient to melt the DNA strands, e.g., 95° C.

After denaturation, the nascent sense primer is allowed to bind to the long, SNAP extension (antisense) product to permit the nucleic acid polymerase to extend the nascent sense primer to yield a long, nascent primer extension (sense) product having a non-target antisense primer binding sequence. The nucleic acid strands are then denatured again. Then, the non-target antisense primer is allowed to bind to the long, nascent primer extension (sense) product to permit the nucleic acid polymerase to extend the non-target antisense primer to yield a short, antisense primer extension (antisense) product terminating in a non-target sense primer binding sequence. The reaction is again subjected to a denaturation step.

Next, the non-target sense primer is allowed to bind to the short primer extension (antisense) product to yield a short non-target primer extension (sense) product terminating in a non-target antisense primer binding sequence. After that step, the non-target primers are allowed to repetitively bind to the short extension products in a series of polymerase extension and denaturation cycles to amplify the target nucleic acid.

In a preferred embodiment, the $T_m$ of the target-specific binding domains for the target sequences is at least 62° C. Furthermore, it is also preferred that the non-target antisense and non-target sense primers have a $T_m$ that is higher than the $T_m$ of the target-specific binding domains for the target sequences. This permits the greater specificity in the amplification stage (after the long, nascent primer extension (sense) product having a non-target antisense primer binding sequence has been synthesized) because the annealing temperature can be raised above the $T_m$ of the target specific primers for the target. This favors annealing and extension of the non-target primers, which results in greater specificity.

The methods for copying a target nucleic acid of the present invention are advantageous in that there is a low level of background signal and normalized hybridization kinetics of primers in the multiplex amplification. Further, fewer primers are required in the amplification of 2 or more different targets as only N+1 instead of 2N primers are required for N targets. Also the same non-target primers can be used for amplification of all targets, which normalizes the hybridization kinetics for all primers and provides high specificity because this non-target primer can be carefully selected to prevent mispriming and primer dimerization.

Because there is only one primer instead of two primes per target present at initial amplification, there is a 1.5 instead of 2 fold amplification in the first cycle. Therefore, the amplification efficiency is $3\times2^{(n-2)}$ for self-primed amplification, while the amplification efficiency is $2^n$ for traditional PCR where n stands for the number of amplification cycles. For amplification of a target RNA in a closed tube format (See Example 3), there is no difference in amplification efficiency between self-primed amplification and PCR.

Amplification of Different Target DNA Sequences

Different target DNA sequences can be amplified in the same reaction vessel using the methods and compositions of the present invention. The same reaction is carried out as for the amplification of a single DNA target, using SNAP primers designed to amplify the different target sequences of interest. The concentration of the magnesium salt in the reaction mixture can be important when trying to copy different target DNA sequences. Thus, some experimentation may be required to optimize the concentration of the magnesium salt, e.g., magnesium chloride, in the reaction to amplify the target nucleic acid sequences of interest. One of skill can vary the concentration of magnesium salt or ion present in the reaction mixture to arrive at the proper conditions for amplification.

Amplification of a Single Target RNA Sequence

A RNA sequence can be amplified using the present invention. The RNA sequence may be present in a naturally or artificially synthesized RNA molecule. For example, the RNA molecule may be total RNA isolated from a cell or RNA that has been synthesized in vitro. Methods for isolating RNA are well known in the art. See, e.g., Ausubel et al. Commercial kits exist for the isolation of total RNA from a cell. See e.g., Maxim Cat No. EXT-0003.

This method permits the amplification of a single target RNA in a closed tube format. This method does not require that the RNA be first reverse transcribed and then added to a reaction vessel for further amplification. Instead, the reverse transcription and amplification steps take place in the same tube. The RNA sample is added to a reaction cocktail comprising: reaction buffer, DTT, DMSO, dNTPs, RNase inhibitor, a reverse transcriptase, and a thermostable DNA Polymerase. Also present in the reaction mixture are SNAP primers and non-target primers. In the first stage, the reaction is incubated at a temperature conducive to reverse transcriptase activity; the nascent primer, a first strand cDNA, is produced in the first stage. The reaction is then temperature cycled through a series of denaturation, annealing, extension steps to permit the production of an amplification product from the first strand cDNA by the DNA polymerase. It is possible for small amounts of an amplification product to be produced when reverse transcriptase is omitted from the reaction. This may be due to reverse transcriptase activity associated with Taq DNA Polymerase. See Shaffer et al. (1990) *Anal. Biochem.* 190(2): 292–296.

Detection of the Amplified Product

Those of skill in the art will recognize that there are many ways to detect nucleic acids. The following are examples of methods used to detect nucleic acids that are subjected to a copying process using the methods and compositions of the present invention.

A. Ethidium bromide staining.

The method of using ethidium bromide to detect DNA in agarose gels is well known in the art. See, e.g., Ausubel et al. Briefly, the amplification products can be electrophoresed on an agarose gel. The agarose gel is then incubated with the intercalating agent, ethidium bromide. The ethidium bromide soaked gel can then be illuminated with ultraviolet light. The ethidium bromide fluoresces under ultraviolet light and permits the visualization of DNA bands in the gel. The molecular size of the product can be estimated by co-electrophoresing a sample with known molecular sizes of DNA, a "DNA ladder." Such DNA ladders are available from a variety of commercial vendors.

B. Fluorescence resonance energy transfer

Methods employing the technique of fluorescence resonance energy transfer (FRET) can be employed using the methods and compositions of the present invention. FRET is a distance-dependent interaction between a donor and acceptor molecule. The donor and acceptor molecules are fluorophores. If the fluorophores have excitation and emission spectra that overlap, then in close proximity (typically around 10–100 angstroms) the excitation of the donor fluorophore is transferred to the acceptor fluorophore.

Hairpin FRET assay

In one particular method employing FRET, fluorescent energy transfer labels are incorporated into a PCR primer that can adopt a hairpin structure. See Nazarenko et al, U.S. Pat. No. 5,866,336; Nadeau et al., U.S. Pat. No. 5,958,700; Tyagi et al., U.S. Pat. No. 5,925, 517. The PCR primers can be designed in such a manner that only when the primer adopts a linear structure, i.e., is incorporated into a PCR product, is a fluorescent signal generated. See Nazarenko et al, U.S. Pat. No. 5,866,336; Nadeau et al., U.S. Pat. No. 5,958,700.

In accordance with the method of U.S. Pat. No. 5,866,336, FRET pairs can be incorporated into the primers of the present invention or into signal oligonucleotides that can be added to the reaction mix, to afford a method of detecting the incorporation of the primer into a polymerization product. The primers of the present invention or the oligonucleotides are able to adopt an intramolecularly base-paired structure (e.g., a hairpin structure). The signal oligonucleotide or the primers of the present invention are modified with two fluorescent dye moieties that form a donor/acceptor dye pair. For example, the donor dye moiety can be fluorescein or a fluorescein derivative and the acceptor can be DABCYL. The two dyes are positioned on the labeled oligonucleotide such that they are in close spatial proximity (typically around 10–100 angstroms) in the base-paired, folded secondary structure. If the dyes are in close spatial proximity then the donor fluorescence is quenched by the acceptor dye.

The signal oligonucleotide or primer comprise a single-stranded target binding sequence and an intramolecularly base-paired secondary structure 5' to the target binding sequence. At least a portion of the target binding sequence forms a single-stranded tail which is available for hybridization to the middle of the amplified target sequence, the signal oligonucleotide having linked thereto a first dye and a second dye such that fluorescence of the first or second dye is quenched. The annealed signal oligonucleotide is extended to produce a signal oligonucleotide extension product. After denaturation, a primer is annealed to the signal oligonucleotide extension product and extended. This linearizes or unfolds the secondary structure and producing a change in a fluorescence parameter. The change in a fluorescence parameter is an indication of amplification of the target sequence.

For example, the single SNAP primers SPAS-BCL-1001 and SPAS-GAP-1001 (SEQ ID NOs: 1 and 2), which have hairpin structures, can be labeled with fluorophores so that incorporation of the SNAP primer results in increased fluorescence. Those of skill in the art will recognize a variety of FRET pairs that can achieve the desired results.

TaqMan assay

The amplification products can be detected in solution using a fluorogenic 5' nuclease assay—The TaqMan assay. See Holland et al., (1991) *Proc. Natl. Acad. Sci, U.S.A.* 88: 7276–7280; Livak et al. U.S. Pat. Nos. 5,538,848, 5,723, 591, and 5,876,930. The TaqMan probe is designed to hybridize to a sequence within the desired PCR product. The 5' end of the TaqMan probe contains a fluorescent reporter dye. The 3' end of the probe is blocked to prevent probe extension and contains a dye that will quench the fluorescence of the 5' fluorophore. During subsequent amplification, the 5' fluorescent label is cleaved off if a polymerase with 5' exonuclease activity is present in the reaction. The excising of the 5' fluorophore results in an increase in fluorescence which can be detected.

A TaqMan probe can be used in conjunction with the present invention. For example, a primer that is labeled with the an appropriate donor/quencher pair and is complementary to a portion of the target nucleic acid sequence between where the target-specific primers bind, can function in the TaqMan assay.

Applications of the Present Invention

The present invention can be used to assay for the presence or absence of target nucleic acids in an analyte. The analyte may be of clinical importance. For example, the analyte may be a sample derived from a patient in a clinical setting. The present invention can be used as a diagnostic tool to test for the presence of a human pathogen or for the amount of a human target nucleic acid. Alternatively, the present invention may be used to test for the presence of a genetic polymorphism in a subject. Still another use of the present invention is to test for the paternity of a subject.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill will readily recognize a variety of noncritical parameters which could be changed or modified to yield essentially similar results.

Example 1

Separate Amplification of Three Different Target cDNAs Using SNAP Primers

Portions of human cDNAs for bcl-xS (Genbank Accession #: L20122), bcl-xL (Genbank Accession #: L20121), and GAPDH (Genbank Accession #: M33197) were amplified from human T cell cDNA or human brain cDNA using SNAP primers. The bcl-xS and bcl-xL are two distinct forms of bcl-x, a bcl-2-related gene that functions as a dominant regulator of apoptotic cell death (Boise et al., (1993) *Cell* 74(4): 597–608). GAPDH is an enzyme involved in glycolysis and catalyzes the transformation of glyceraldehyde 3-phosphate into 1,3-bisphosphoglycerate. GAPDH can be used as an internal control for the amount of target nucleic acid added to a reaction, as GAPDH is a housekeeping gene. See Ercolani et al., (1988) *J Biol. Chem.* 263(30): 15335–15541.

A. Source of cDNAs.

The human T-cell cDNA was obtained from Maxim, Catalogue #: PCR-8025. That product is total RNA from human T cells that has been reverse transcribed into double-stranded cDNA. The human brain cDNA was obtained from Maxim, Catalogue #: PCR-8002. That product is total RNA from human brain that has been reverse transcribed into double-stranded cDNA.

B. Description of primers used in the amplification reactions.

The SNAP primer used to amplify bcl-xS and bcl-xL was SEQ ID NO: 1 and is denoted SPAS-BCL-1001 (5' CAG TTC AAA CTC GTC GCC TGC CTA GTC GAC ACG TGT ACG ACG TCG ACG TCG TAC ACG TGT CGA CTC AGG AAC CAG CGG TTG AAG CGT 3'). The four domains of the SPAS-BCL-1001 primer are delineated in FIG. 2. Domains i and iv correspond to nucleotides #569–591 and #409–431 of the bcl-xS gene (Genbank Accession #: L20122). Domains i and iv of the SPAS-BCL-1001 primer are complementary to nucleotide positions #758–780 and #409–431 of the bcl-xL gene (Genbank Accession #: L20121). Domains i and iv of SPAS-BCL-1001 have a $T_m$'s of 70° C. for the target sequences on bcl-xS and bcl-xL. The $T_m$'s of the SPAS-BCL-1001, SPAS-GAP-1001 and ADP-1002 for their corresponding sequences were calculated using a nearest-neighbor interaction model. See Breslauer, et al. (1986) *Proc. Natl. Acad. Sci. U.S.A.* 83: 3746–3750; Allawi and SantaLucia (1997) *Biochemistry* 36: 10581–10594.

The human GAPDH cDNA was amplified with the SNAP primer denoted SPAS-GAP-1001 (SEQ ID NO: 2: 5' GAC TCC GAC CTT CAC CTT CAG TCG ACA CGT GTA CGA CGT CGA CGT CGT ACA CGT GTC GAC TCA AAG TTG TCA TGG ATG ACC 3'). The four domains of the SPAS-GAP-1001 primer are delineated in FIG. 2. Domains i and iv correspond to nucleotides #546–565 and #66–84 of GAPDH gene (Genbank Accession #: M33197). Domains i and iv of the SPAS-GAP-1001 have $T_m$'s of 63° C. for the corresponding sequences on the GAPDH gene.

The adaptor primer is ADP-1002 (SEQ. ID. NO. 3; 5' GACGTCGACGTCGTACACGTGTCGACT3'). This sequence is complementary to domain iii of SPAS-GAP-1001 and SPAS-BCL-1001, and has identity to domains ii of SPAS-GAP-1001 and SPAS-BCL-1001. ADP-1002 has a $T_m$ of 75.4° C. between ADP-1002 and its complementary sequence (either domain ii or iii). The expected sizes of the amplification product for bcl-xL and bcl-xS are 426 bp and 237 bp, respectively. The expected size of the GAPDH amplification product is 554 bp.

C. Amplification Reaction.

The amplification reaction cocktail is made up of reaction buffer, deoxynucleotidetriphosphates, and Taq DNA Polymerase. The reaction buffer used in the amplification reaction contains 20 mM Tris-HCl, pH 8.3, 50 mM KCl, 2.5 mM $MgCl_2$ and 0.1% BSA. Deoxynucleotidetriphosphates were added to a final concentration of 0.25 mM each. Approximately 2 Units of Taq DNA Polymerase (Promega) were added for a 50 $\mu$l reaction.

The cDNA (human brain cDNA or human T cell cDNA) were present at about 10 ng per 50 $\mu$l reaction mixture. The primers were added to the reaction mixture in the absence and presence of ADP-1002 with the respective cDNAs. The SNAP primers were used at a final concentration of 0.01 $\mu$M and the ADP-1002 primer was used at a final concentration of 0.2 $\mu$M. Six reactions were carried out. The primer combinations and cDNAs in each reaction were shown in Table I, supra.

The reaction was incubated in a GeneAmp PCR System 2400 (Perkin Elmer) in four successive stages. In the first stage, the reactions were subjected to 5 cycles where the temperature was held at 95° C. for 1 min., then shifted to 56° C for 4 min. In the second stage, the reactions were subjected to 27 cycles where the temperature was held at 94° C. for 1 min., then shifted to 68° C. for 2 min. In the third stage, the reactions were held at 72° C. for 10 min. In the fourth stage the reaction was held at 20° C. until the reaction was ready to be analyzed.

D. Results

Figure 4:
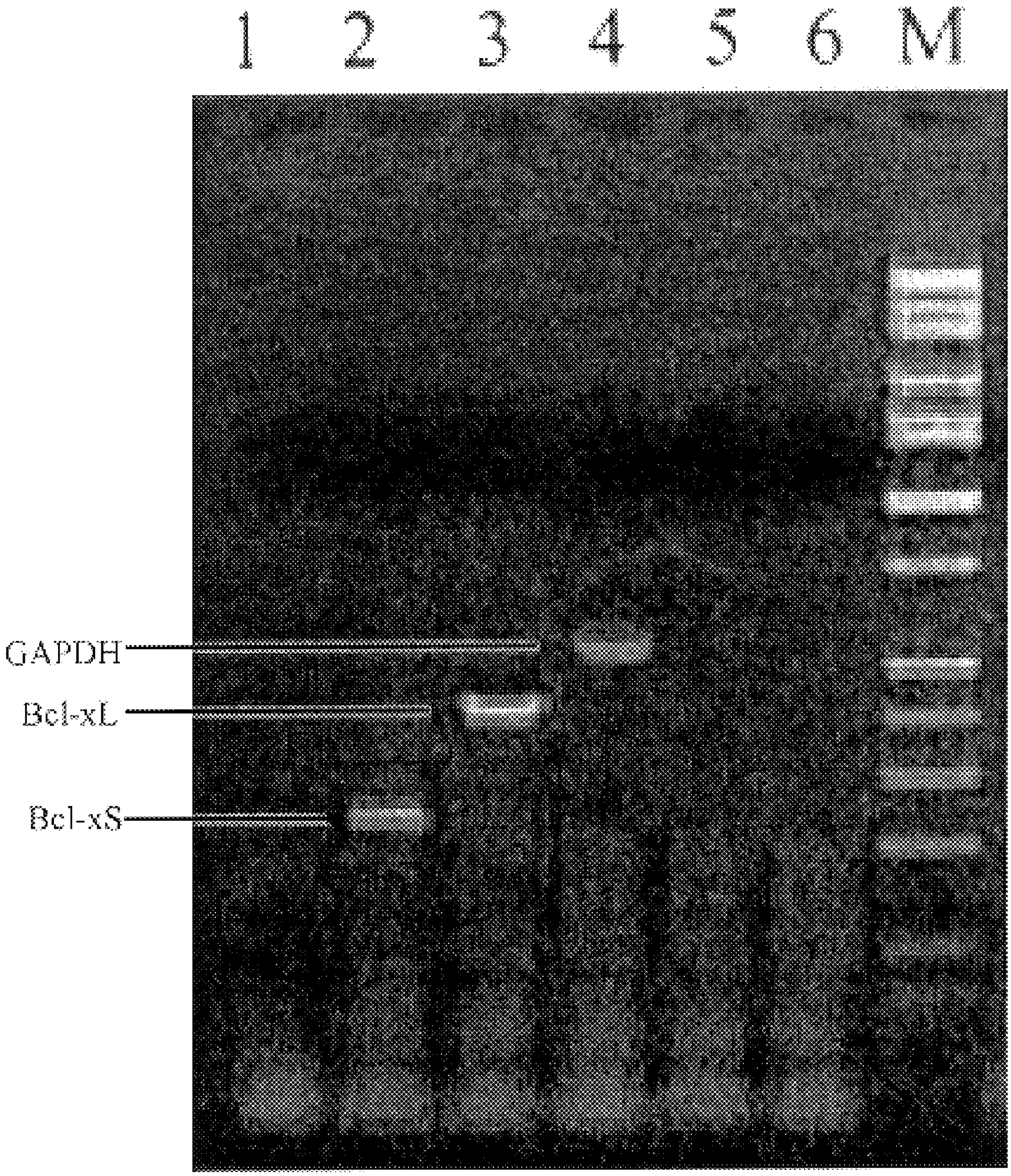
FIG. 4 is a gel photograph of the separate amplification of human T cell cDNA or human brain cDNA using SNAP primers that target bcl-xS, bcl-xL or GAPDH sequences. The reactions were separately amplified and electrophoresed on a 2% agarose gel. The gel was stained with ethidium bromide. The primer and cDNA components for the respective lanes are shown in Table I. The lane denoted "M" is a marker lane containing a DNA ladder (Minnesota Molecular Hi-Lo™ DNA Marker, Cat. No. 1010).

After the reactions were stopped, they were electrophoresed on a 2% agarose gel. A DNA ladder (Minnesota Molecular Hi-Lo™ DNA Marker, Cat. No. 1010) was electrophoresed with the reactions as a molecular weight standard. The gel was then stained with ethidium bromide and a photograph was taken of the gel on an ultra-violet light box. See FIG. 4. There was no product observed in reactions that did not contain both a SNAP primer and the ADP-1002 primer. See FIG. 2, Lanes 1, 5 and 6. Amplification of the human T cell cDNA with SPAS-BCL-1001 and ADP-1002 gave rise to a band consistent with the 237 bp product that was expected for bcl-xS. See FIG. 2, Lane 2. Likewise the amplification of human brain cDNA produced a band (FIG. 2, lane 3) of the expected size of 426 bp for bcl-xL. The GAPDH sequence was also amplified from human T cell cDNA with the expected molecular size (554 bp). See FIG. 4, Lane 4. Thus, 3 different targets can be amplified separately using SNAP primers and an adaptor primer. Similar results were obtained using isolated human cDNA clones for bcl-xS, bcl-xL and GAPDH.

Example 2

Co-amplification of Different Target cDNAs Using SNAP Primers.

The amplification reaction cocktail used in this experiment was the same as in Example 1, except the reaction buffer (20 mM Tris-HCl, pH 8.3, 50 mM KCl, and 0.1% BSA) with different $MgCl_2$ concentrations (from 1.5 mM to 3.5 mM) were used. In this example, 10 ng of human T cell cDNA and 10 ng of human brain cDNA along with the SPAS-BCL-1001, SPAS-GAP-1001, and ADP-1002 primers were added to the amplification reaction cocktail. See Table II. The reactions were incubated at the same temperatures and times as in Example 1. The reactions were electrophoresed and incubated with ethidium bromide as in Example 1.

Three bands were produced at the expected sizes for the bcl-xS (237 bp), bcl-xL (426 bp) and GAPDH (554 bp) reaction products under the condition of 2.5 mM and 3.5 mM $MgCl_2$. See FIG. 5, Lanes 3 and 4, respectively. No product was seen under the condition of 1.5 mM $MgCl_2$ or without cDNAs. See FIG. 5, Lanes 2 and 1, respectively. So, the amplification of different target cDNAs may require some optimization of the magnesium concentration to achieve the desired results. Thus, the present invention can be used to amplify different DNA targets in a single reaction.

Example 3

Reverse transcription and subsequent amplification of a single target RNA using a SNAP primer.

A. Isolation of keratinocyte total RNA.

The total RNAs from the cultured keratinocytes were isolated using a RNA isolation kit (Maxim, Cat No. EXT-0003).

B. Amplification Reaction.

The amplification reaction cocktail is made up of reaction buffer, DTT, DMSO, deoxynucleotidetriphosphates, *C. therm* Polymerase (Roche) and Taq DNA Polymerase. The reaction buffer used in the amplification reaction contains 0.5×Reverse Transcriptase Buffer (Roche), 5 mM DTT, 5% DMSO. Deoxynucleotidetriphosphates were added to a final concentration of 0.25 mM each. Approximately 2 U of *C. therm* Polymerase (Roche, Cat. No. 2016311) and 2 U of Taq DNA Polymerase (Promega) were added for a 50 μl reaction. 75 U of RNase inhibitor (Amersham) was added for a 50 μl reaction.

The total RNAs from the cultured keratinocytes were present at amount of 1 μg per 50 μl reaction mixture. The SNAP primers were used at a final concentration of 0.01 μM and the ADP-1002 primer was used at a final concentration of 0.2 μM. See Table III.

The reaction was incubated in a GeneAmp PCR System 2400 (Perkin-Elmer) in five successive stages. In the first stage, the reaction was subjected to an incubation where the temperature was held at 58° C for 30 min. In the second stage, the reactions were subjected to 5 cycles where the temperature was held at 95° C. for 1 min., then shifted to 56° C. for 4 min. In the third stage, the reactions were subjected to 27 cycles where the temperature was held at 94° C. for 1 min., then shifted to 68° C. for 2 min. In the fourth stage, the reactions were held at 72° C. for 10 min. In the fifth stage the reaction was held at 20° C. until the reaction was ready to be analyzed.

A band was produced at the expected sizes for GAPDH (554 bp) reaction products in presence of *C. therm* Polymerase and Taq DNA Polymerase and all primers. There is a faint band at the expected size for the GAPDH (554 bp) reaction product in the presence of only Taq DNA Polymerase and all primers, which could be due to reverse transcriptase activity associated with Taq DNA Polymerase (Shaffer et al., (1990) *Anal. Biochem.* 190(2): 292–296). See FIG. 6, Lane 3. Thus, the present invention can be used to amplify RNA targets directly in a closed tube format.

What is claimed is:

1. A self-priming nucleic acid polymerase (SNAP) primer for copying a target nucleic acid comprising four domains of nucleic acid sequences in the following order from 3' to 5':

i. a sense, target-specific binding domain;

ii. a non-target, antisense primer binding domain;

iii. a non-target sense primer binding domain;

iv. an antisense, target-specific binding domain, wherein the sequence of the domain complements a sense sequence of the target which lies upstream of the target sequence complementary to the sense, target-specific binding domain.

2. The primer of claim 1, wherein the antisense, target-specific binding domain has sequence identity with the antisense sequence of the target nucleic acid.

3. The primer of claim 1, wherein said target nucleic acid is comprised of a sequence from a human or a human pathogen.

4. The primer of claim 1, wherein the $T_m$ for the sense, target-specific binding domain or the antisense, target-specific binding domain and their complementary sequences on said target nucleic acid is at least 62° C.

5. The primer of claim 1, wherein the non-target, antisense primer binding domain or the non-target, sense primer binding domain bind to a DNA comprising its complementary sequence at a $T_m$ that is higher than the $T_m$ for the target-specific binding domain and its complementary sequence on said DNA.

6. The primer of claim 1, wherein the anti-sense, target-specific binding domain binds to a DNA comprising its complementary sequence with a $T_m$ that is about the same as the $T_m$ for the sense, target-specific binding domain and its complementary sequence on said DNA.

7. The primer of claim 1, wherein said non-target, antisense primer binding domain and said non-target, sense primer binding domain are the same but in opposite orientation.

8. The primer of claim 1, wherein said domains iii and iv can generate a nascent primer in the presence of a non-target primer and a polymerase in an amplification reaction.

9. The primer of claim 1, wherein the non-target, antisense primer binding domain and the non-target sense primer binding domain are different sequences.

10. A mixture of amplification primers composed of first and second primers for copying a target nucleic acid, (a) said first primer comprising two domains of nucleic acid sequences in the following order from 3' to 5':

i. a sense, target-specific binding domain;

ii. a non-target, antisense primer binding domain;

(b) said second primer comprising two domains of nucleic acid sequences in the following order from 3' to 5':

i. a non-target sense primer binding domain;

ii. an antisense, target-specific binding domain wherein the sequence of the domain complements a sense sequence of the target nucleic acid which lies upstream of the target nucleic acid sequence complementary to the sense, target-specific binding sequence.

11. The mixture of claim 10, wherein said second primer is comprised of RNA.

12. The mixture of claim 10, wherein the 3' end of said second primer is blocked.

13. A mixture of nucleic acid primers for copying a target nucleic acid comprising a primer mixture selected from the group consisting of:

(a) a primer comprising two domains of nucleic acid sequences in the following order from 3' to 5':

i. a sense, target-specific binding domain;

ii. a non-target, antisense primer binding domain; and a primer having 3' sequence identity to the sequence of the non-target, antisense primer binding domain;

(b) a primer comprising two domains of nucleic acid sequences in the following order from 3' to 5':

i. a non-target sense primer binding domain;

ii. an antisense, target-specific binding domain wherein the sequence of the domain complements a sense sequence of the target nucleic acid which lies upstream of the target nucleic acid sequence complementary to the sense, target-specific binding sequence; and a primer complementary to the non-target sense primer binding domain; and (c) a combination of the above four primers.

14. The mixture of claim 13, wherein the primer complementary to the sequence of the non-target, antisense primer binding domain and the primer complementary to the sequence of the non-target sense primer binding domain are identical.

15. The mixture of claim 13, wherein said second primer is comprised of RNA.

16. The mixture of claim 13, wherein the 3' end of said second primer is blocked.

17. A method of copying a target nucleic acid said method comprising:

(a) combining in an aqueous solution: a target nucleic acid, a nucleic acid polymerase, a molar excess of dNTP, a non-target antisense-primer, a non-target sense-primer, and self-priming nucleic acid polymerase (SNAP) primers for copying a target nucleic acid, the primers comprising four domains of nucleic acid sequences in the following order from 3' to 5':

i. a sense, target-specific binding domain;

ii. a non-target, antisense primer binding domain;

iii. a non-target sense primer binding domain;

iv. an antisense, target-specific binding domain, wherein the sequence of the domain complements a sense sequence of the target nucleic acid which lies upstream of the target nucleic acid sequence complementary to the sense, target-specific binding sequence;

wherein domains i and ii are joined together to form a first primer and domains iii and iv are joined together to form a second primer or wherein i, ii, iii, and iv are all joined together to form a single primer;

(b) allowing the SNAP primers to bind to the target nucleic acid and to the non-target sense primer, to permit the nucleic acid polymerase to extend the primers to create:

i. a nascent sense primer having a non-target primer sequence and a target-specific binding sequence having identity to a sense sequence of the target nucleic acid which lies upstream of the target nucleic acid sequence complementary to the sense, target-specific binding sequence of the SNAP primer; and ii. a long SNAP extension (antisense) product;

(c) denaturing the nucleic acid strands;

(d) allowing the nascent sense primer to bind to the long, SNAP extension (antisense) product to permit the nucleic acid polymerase to extend the nascent sense primer to yield a long, nascent primer extension (sense) product having a non-target antisense primer binding sequence;

(e) denaturing the nucleic acid strands;

(f) allowing the non-target antisense primer to bind to the long, nascent primer-extension (sense) product to permit the nucleic acid polymerase to extend the non-target antisense primer to yield a short, antisense primer extension (antisense) product terminating in a non-target sense primer binding sequence;

(g) denaturing the nucleic acid strands;

(h) allowing the non-target sense primer to bind to the short primer extension (antisense) product to yield a short non-target primer extension (sense) product terminating in a non-target antisense primer binding sequence; and (i) repetitively allowing the non-target primers to bind to the short extension products in a series of polymerase extension and denaturation cycles to amplify the target nucleic acid.

18. The method of claim 17, wherein said step (a) further comprises denaturing the nucleic acid strands.

19. The method of claim 17, wherein the SNAP primer comprises in a single nucleic acid four domains of nucleic acid sequences in the following order from 3' to5':

i. a sense, target-specific binding domain;

ii. a non-target, antisense primer binding domain;

iii. a non-target sense primer binding domain;

iv. an antisense, target-specific binding domain, wherein the sequence of the domain complements a sense sequence of the target nucleic acid which lies upstream of the target nucleic acid sequence complementary to the sense, target-specific binding sequence.

20. The method of claim 17, wherein the concentration of SNAP primers is at least 10 fold lower than the concentration of non-target primers.

21. The method of claim 17, wherein the extension cycles of step (i) occur at a higher temperature than the first polymerase extension in step (b).

22. The method of claim 17, wherein said target nucleic acid is DNA.

23. The method of claim 17, wherein said target nucleic acid is DNA that has been reverse transcribed from RNA.

24. The method of claim 17, wherein said second primer is comprised of RNA.

25. The method of claim 17, wherein said nucleic acid polymerase of step (b) is a reverse transcriptase.

26. The method of claim 17, wherein the nascent primer is formed by a DNA polymerase and the long SNAP extension (antisense) product is formed by a reverse transcriptase.

27. The method of claim 17, wherein at least 3 different SNAP primers are used in the same solution.

28. The method of claim 27, wherein at least 3 different target nucleic acids are simultaneously copied in the same solution.

29. A method for copying at least 2 different target nucleic acids comprising (a) combining in an aqueous solution: at least 2 different target nucleic acids, nucleic acid polymerase, a molar excess of dNTPs, non-target antisense primers, non-target sense-primers, and self-priming nucleic acid polymerase (SNAP) primers for copying at least 2 different target nucleic acids, the primers comprising four domains of nucleic acid sequences in the following order from 3' to 5':

i. a sense, target-specific binding domain;

ii. a non-target, antisense primer binding domain;

iii. a non-target sense primer binding domain;

iv. an antisense, target-specific binding domain, wherein the sequence of the domain complements a sense sequence of the target nucleic acid which lies upstream of the target nucleic acid sequence complementary to the sense, target-specific binding sequence;

wherein domains i and ii are joined together to form a first primer and domains iii and iv are joined together to form a second primer, or wherein i, ii, iii, and iv are all joined together to form a single primer;

(b) allowing the SNAP primers to hybridize to said at least 2 different target nucleic acids and to the non-target sense primers, to permit the nucleic acid polymerase to extend the primers to create:

i. nascent sense primers having a non-target primer sequence and a target-specific binding sequence having identity to a sense sequence of the target nucleic acid which lies upstream of the target nucleic acid sequence complementary to the sense, target-specific binding sequence of the SNAP primer; and ii. long SNAP extension (antisense) products;

(c) denaturing the nucleic acid strands;

(d) allowing the nascent sense primers to bind to the long, SNAP extension (antisense) products to permit the nucleic acid polymerase to extend the nascent sense primers to yield long, nascent primer extension (sense) products having a non-target antisense primer binding sequence;

(e) denaturing the nucleic acid strands;

(f) allowing the non-target antisense primers to bind to the long, nascent primer extension (sense) products to permit the nucleic acid polymerase to extend the non-target antisense primers to yield a short, antisense primer extension (antisense) products terminating in a non-target sense primer binding sequence;

(g) denaturing the nucleic acid strands;

(h) allowing the non-target sense primer to bind to the short primer extension(antisense) product to yield a short non-target primer extension (sense) product terminating in a non-target antisense primer binding sequence; and (i) repetitively allowing the non-target primers to bind to the short extension products in a series of nucleic acid polymerase extension and denaturation cycles to amplify the target nucleic acid.

30. The method of claim 29, wherein said target nucleic acids are contained in a lysate.

31. The method of claim 29, wherein said method further comprises a detecting step.

32. The method of claim 31, wherein said detecting step occurs in a homogenous assay.

33. The method of claim 29, wherein said non-target antisense primer or said non-target sense-primer include a detectable label.

34. The method of claim 33, wherein said detectable label is a fluorescent label.

35. The method of claim 29, wherein said step (a) further comprises denaturing the nucleic acid strands.

36. The method of claim 29, wherein said second primer is comprised of RNA.

37. The method of claim 29, wherein the 3' end of said second primer is blocked.

38. The method of claim 29, wherein said target nucleic acid is DNA.

39. The method of claim 29, wherein said target nucleic acid is DNA that has been reverse transcribed from RNA.

40. The method of claim 29, wherein the nascent primer is formed by a DNA polymerase and the long SNAP extension (antisense) product is formed by a reverse transcriptase.

41. The method of claim 29, wherein at least 3 different SNAP primers are used in the same solution.

42. The method of claim 29, wherein at least 3 different target nucleic acids are simultaneously copied in the same solution.

43. The method of claim 29, wherein the SNAP primer comprises in a single nucleic acid four domains of nucleic acid sequences in the following order from 3' to 5':

i. a sense, target-specific binding domain;

ii. a non-target, antisense primer binding domain;

iii. a non-target sense primer binding domain;

iv. an antisense, target-specific binding domain, wherein the sequence of the domain complements a sense sequence of the target nucleic acid which lies upstream of the target nucleic acid sequence complementary to the sense, target-specific binding sequence.

44. The method of claim 29, wherein said target nucleic acids are comprised of a at least one sequence from a human or a human pathogen.

45. The primer of claim 1, wherein said primer has the sequence of SEQ ID NO: 1.

46. The primer of claim 1, wherein said primer has the sequence of SEQ ID NO: 2.

47. The primer of claim 1, wherein said primer is a component of a kit.

48. A kit comprising:

a container having a self-priming nucleic acid polymerase (SNAP) primer for copying a target nucleic acid comprising four domains of nucleic acid sequences in the following order from 3' to 5':

i. a sense, target-specific binding domain;

ii. a non-target, antisense primer binding domain;

iii. a non-target sense primer binding domain;

iv. an antisense, target-specific binding domain, wherein the sequence of the domain complements a sense sequence of the target nucleic acid which lies upstream of the target nucleic acid sequence complementary to the sense, target-specific binding sequence;

wherein domains i and ii are joined together to form a first primer and domains iii and iv are joined together to form a second primer or wherein i, ii, iii, and iv are all joined together to form a single primer.

49. The kit of claim 48, wherein said kit further comprises at least two non-identical said self-priming nucleic acid polymerase (SNAP) primers.

50. The kit of claim 48, wherein said sense, target-specific binding domain or said antisense, target-specific binding domain are complementary to a sequence from a human or a human pathogen.

51. The kit of claim 48, wherein said kit further comprises a non-target antisense primer or a non-target sense-primer.

52. The kit of claim 48, wherein said non-target antisense primer and said non-target sense-primer have the same sequence.

* * * * *

SEQUENCE LISTING

```
<160> NUMBER OF SEQ ID NOS:  3

<210> SEQ ID NO 1
<211> LENGTH: 87
<212> TYPE: DNA
<213> ORGANISM: Artificial Sequence
<220> FEATURE:
<223> OTHER INFORMATION: Description of Artificial Sequence:single
      self-priming nucleic acid polymerase (SNAP) primer
      SPAS-BCL-1001 directed toward bcl-xS and bcl-xL
```

-continued

```
      sequences

<400> SEQUENCE: 1

cagttcaaac tcgtcgcctg cctagtcgac acgtgtacga cgtcgacgtc gtacacgtgt     60

cgactcagga accagcggtt gaagcgt                                         87


<210> SEQ ID NO 2
<211> LENGTH: 81
<212> TYPE: DNA
<213> ORGANISM: Artificial Sequence
<220> FEATURE:
<223> OTHER INFORMATION: Description of Artificial Sequence:single
      self-priming nucleic acid polymerase (SNAP) primer
      SPAS-GAP-1001 directed toward
      glyceraldehyde-3-phosphate dehydrogenase (GAPDH)

<400> SEQUENCE: 2

gactccgacc ttcaccttca gtcgacacgt gtacgacgtc gacgtcgtac acgtgtcgac     60

tcaaagttgt catggatgac c                                               81


<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:adaptor
      primer ADP-1002

<400> SEQUENCE: 3

gacgtcgacg tcgtacacgt gtcgact                                         27
```